(12) United States Patent
Dickinson et al.

(10) Patent No.: US 7,270,004 B2
(45) Date of Patent: Sep. 18, 2007

(54) METHOD AND APPARATUS FOR CARRYING OUT NON-DESTRUCTIVE TESTING OF MATERIALS

(75) Inventors: Laurence Dickinson, Carlingford (AU); Suszanne Thwaites, deceased, late of Lindfield (AU); by Vivonne Thwaites, legal representative, Henley Beach (AU)

(73) Assignee: Commonwealth Scientific and Industrial Research Organisation, Campbell ACT (AU)

( * ) Notice: Subject to any disclaimer, the term of this patent is extended or adjusted under 35 U.S.C. 154(b) by 0 days.

(21) Appl. No.: 10/474,885

(22) PCT Filed: Apr. 19, 2002

(86) PCT No.: PCT/AU02/00501

§ 371 (c)(1),
(2), (4) Date: Dec. 10, 2004

(87) PCT Pub. No.: WO02/086484

PCT Pub. Date: Oct. 31, 2002

(65) Prior Publication Data

US 2006/0048578 A1     Mar. 9, 2006

(30) Foreign Application Priority Data

Apr. 20, 2001   (AU) .................................. PR4508

(51) Int. Cl.
*G01N 29/42*   (2006.01)
(52) U.S. Cl. ............................ 73/602; 73/579; 73/599; 73/628

(58) Field of Classification Search ................. 73/602, 73/579, 597, 598, 599, 600, 627, 628
See application file for complete search history.

(56) References Cited

U.S. PATENT DOCUMENTS 4,482,889 A    11/1984  Tsuda et al.

(Continued)

FOREIGN PATENT DOCUMENTS

| EP | 0294255 | 5/1988 |
|----|---------|--------|
| EP | 0574963 | 12/1993 |

OTHER PUBLICATIONS

Derwent Abstract Accession No. 2000-003256/01, Class S03 JP 11-281629 A (Nippon Steel Corp) Oct. 15, 1999 See abstract.

(Continued)

*Primary Examiner*—Hezron Williams
*Assistant Examiner*—Jacques M Saint-Surin
(74) *Attorney, Agent, or Firm*—Ladas & Parry LLP

(57) ABSTRACT

A method of testing a material sample for defects, comprising the steps of applying a test signal to the material sample, receiving a return signal from the material sample and analysing the return signal to determine whether the material sample is defective. In one aspect of the present invention the steps of receiving a return signal and analysing it include the step of selecting a frequency range to reduce the effect of potentially interfering signals. In another aspect of the present invention a reference signal obtained from a non-defective sample is subtracted from the return signal to give a difference result and the difference result is indicative of whether the material sample is defective. Apparatus for carrying out the above-defined methods are also provided.

14 Claims, 7 Drawing Sheets

U.S. PATENT DOCUMENTS

| | | | | |
|---|---|---|---|---|
| 4,736,130 | A | * | 4/1988 | Puskas ................. 310/316.01 |
| 4,743,789 | A | * | 5/1988 | Puskas ................. 310/316.01 |
| 4,792,755 | A | | 12/1988 | Huschelrath et al. |
| 4,869,109 | A | * | 9/1989 | Miglianico et al. ........... 73/602 |
| 5,623,100 | A | * | 4/1997 | Arima et al. ................. 73/611 |
| 5,671,154 | A | * | 9/1997 | Iizuka et al. ................. 702/39 |
| 6,301,967 | B1 | * | 10/2001 | Donskoy et al. ............. 73/579 |
| 6,421,811 | B1 | * | 7/2002 | Goruganthu et al. ........... 716/4 |
| 6,581,014 | B2 | * | 6/2003 | Sills et al. .................... 702/39 |
| 6,684,701 | B2 | * | 2/2004 | Dubois et al. ............... 73/579 |
| 6,747,268 | B1 | * | 6/2004 | Ume .................... 250/227.11 |
| 6,799,126 | B1 | * | 9/2004 | Ratcliffe et al. .............. 702/56 |
| 7,004,016 | B1 | * | 2/2006 | Puskas ..................... 73/64.53 |
| 7,107,825 | B2 | * | 9/2006 | Degertekin et al. ........... 73/105 |

OTHER PUBLICATIONS

Derwent Abstract Accession No. 96-071824/08, Class S03 JP 07294500- A (Hitachi Constr Machinery Co Ltd) Nov. 10, 1995 See abstract.

Derwent Abstract Accession No. 86-284110/43, Class S03 SU 1221594 A (Ind Prog Automn) Mar. 30, 1986 See abstract.

* cited by examiner

METHOD AND APPARATUS FOR CARRYING OUT NON-DESTRUCTIVE TESTING OF MATERIALS

FIELD OF INVENTION

The present invention relates to a method and apparatus for the non-destructive testing of materials and, particularly, but not exclusively, to a method and apparatus for non-destructive testing of composite materials.

BACKGROUND OF THE INVENTION

Non-destructive testing (NDT) may be used to test composite materials, such as aeroplane panels, for mechanical defects. Defects can be caused by stress on materials or mechanical damage from the impact of objects on panels or defective manufacture.

The ability to test these materials in situ is very important. Regular testing is obviously required for safety, particularly in the aeroplane industry, and it is impractical to disassemble aircraft or parts of aircraft to carry out testing.

One preferred method of NDT is to utilise a probe to excite the test material or structure with radiation (generally, but not exclusively, acoustic and near acoustic frequencies are used for NDT) and detect a response. The response can be indicative of whether the test sample is faulty or not "defected". Usually the response is compared with a response from similar excited radiation of a reference material or structure, which will usually be an undefected composite of the same type as the test material, but may also be a composite having reference defects.

Determination of whether there is a defect in the test material usually involves merely the comparison of the output waveform provided by the detection electronics with the response signal waveform of the reference material (which may in some cases, for example, be an undefected area of the same aircraft—where it is an aircraft panel which is being tested).

Acoustic or Ultrasound frequencies used to excite the materials are typically in the range of 5 to 70 kHz.

One of the most popular known NDT systems utilises the pitch/catch impulse test. A typical pitch/catch probe comprises 2 spring-loaded (or otherwise resiliently mounted) contact tips set approximately 10 mm apart which are held in contact with the test sample. These are equipped with 2 actuators, one of which generates a mechanical vibration within the above frequency range and the other of which detects the response. The drive signal is generally a short wave train, up to 6 cycles of sinusoidal impulse (or similar). The detector measures the response of the test sample at its contact point. The propagation of the disturbance from the driver to the detector is influenced by the nature of the intervening structure and in particular, by any damage or anomaly in this region. It is therefore (in theory) possible to obtain information concerning mechanical defects in a non-destructive manner. With composite materials in particular defects may also include failure of adhesion i.e. a disbond or delamination. NDT is used to detect any defect, including disbonds and delaminations and other damages of the material itself or of rivets and joints etc.

To initially calibrate the apparatus and select drive frequency, the drive frequency is chosen so as to optimise the difference in received signal between a faulty sample and an undefected sample. The frequency is usually selected to provide the maximum output from the detector electronics.

It has been found that the performance of presently available NDT systems of this type is not good. Often it is difficult to determine with accuracy whether a defect exists or not in a test sample. Further, the present systems comprise complex and expensive hardware. They also require a relatively high level of skill to be able to operate them and interpret the results.

It would be desirable to be able to provide a method and apparatus which provides a more reliable detection of defects in test samples than in the prior art, which generally improves and simplifies the analysis of the NDT data, and in which the NDT apparatus is relatively simple and inexpensive.

SUMMARY OF THE INVENTION

In accordance with a first aspect of the present invention, there is provided a method of testing a material sample for defects, comprising the steps of applying a test signal to the material sample, receiving a return signal from the material sample and analysing the waveform of the return signal to determine whether the material sample is defective, and wherein the steps of receiving a return signal and analysing it include the step of selecting a frequency range to reduce the effect of potentially interfering signals.

The applicants have discovered by experiment with prior art NDT systems that the available pitch/catch probes have internal structural resonances associated with the dimensions of the driver and receive transducers, the contact tips and the housing (some other types of prior art probes may also have similar problems). These resonances occur throughout the range 15 to 60 kHz.

In other prior art probes, however, it is possible that resonances may occur at other frequencies. Resonances may also occur below 3 kHz in present probes.

Further, the applicants have undertaken experiments which show that for most composite panels used as test samples there is a strong local vibration response over a defect in the range of 5 to 50 kHz. Typical materials are carbon or glass fibre reinforced plastics in a sandwich construction with skins of these materials and a core of Nomex or foam. Skin thicknesses can be in the range from fractions of millimetres to several millimetres and core thickness is in the range of 5 to 50 mm or even thicker.

In the prior art, therefore, the frequency range of defected sample responses and the frequency range containing the pitch/catch probe resonances substantially overlap. In addition, the applicants have found that the output generated by the probe resonances is considerably larger (by a factor usually 10 to 20 times) than the output generated by the defect. In the prior art, the drive frequency is chosen, according to manufacturers instructions, so as to optimise the difference in received signal between undefected and defected panels. As a consequence the set up process biases the users strongly towards frequencies in the range 20 to 30 kHz.

It is believed by the applicant, therefore, that the probe resonances of the frequencies utilised in prior art systems lead to difficulty in determining from signals whether defects actually do or do not exist in the samples.

The present invention includes the novel step of selecting a frequency range which at least reduces the effect of these potentially interfering signals on the return signal. The prior art methods appear to have been unaware of these potentially interfering signals.

A frequency range of between 1 and 20 kHz preferably is selected and, more preferably, between 1 and 22 kHz. For a typical composite material, most preferably a range of between 3 and 15 kHz is selected. Note that other ranges may be selected, however, where interfering signals occur in other frequency ranges than in typical probes. In general, there appears to be the tendency that materials that are of lower density have a higher frequency range within which interfering signals are substantially reduced. For example, for aluminium it has been observed that within a frequency range of 18 to 22 kHz interfering signals are substantially reduced and for this material this frequency range therefore most preferably is selected.

The present applicant, by selecting the above discussed frequency range for the received signal, leaves a range where there is a minimum overlap of defect and probe response and existence of defects can be determined accurately.

Preferably, the test signal is also selected to be within the range 1 to 20 kHz and more preferably within the range ol to 22 kHz. For example for a typical composite material the test signal most preferably is selected within the range of 3 to 15 kHz and for aluminium the test signal most preferably is selected within the range of 18 to 22 kHz. In a preferred embodiment, the test signal is generally chosen to be approximately 2 cycles at approximately 10 kHz. This is a fairly broadband excitation which ensures that plenty of energy is supplied within the most preferred frequency ranges.

In order to select the preferred range of return signal processing, the return signal is preferably bandpass filtered between 3 and 15 kHz or between 18 and 22 kHz with a very high Q filter (8 pole). This preferably eliminates both low frequency noise from environmental structural sources and all probe resonances above the upper limit of the frequency range. It leaves a range where there is a minimum overlap of defect and probe response (note that this range may be varied depending upon where the interfering frequencies are occurring).

One of the other problems of the prior art is presentation of the information once the signal has been processed.

Preferably, in the present invention the method comprises the further step of taking a reference signal which has been obtained from a non-defective sample and subtracting the reference signal from the return signal, to give a difference result.

Preferably, the difference result is displayed.

This step has the advantage that a user is easily able to determine from the difference result that a defect exists, and also is preferably able to determine the relative extent of the defect (depending upon the size of the difference result).

Preferably, the reference signal and return signal are digitised before the subtraction operation. The subtraction operation preferably is performed in the frequency domain and the signal may also be digitally filtered. A computer routine most preferably is used to perform the subtraction. Preferably, the difference result is provided as a difference number which is calculated by summing the absolute value of the point by point difference over the whole or some user selected part of the return signal versus reference signal. This yields a single number for each sample position on the test piece, which is known here as the "damage index". An electronic library of saved response signals may be used to facilitate identification of a defect.

Preferably, utilising the damage index, a map across the test piece is presented on a display for viewing by the user.

Preferably, the method of the present invention is implemented by software utilising a computing system. Input to the system is from a pitch/catch probe. The computing system may be a standard computing system such as a personal computer or laptop, adapted by any additional signal processing hardware that may be required. This is may be cheaper and more convenient than the complex and expensive hardware required for prior art systems.

In accordance with a second aspect of the present invention there is provided a method of testing a material sample for defects comprising the steps of applying a test signal to the material sample, receiving a return signal from the material sample, taking a reference signal obtained from a non-defective sample and subtracting the reference signal from the return signal to give a difference result, whereby the difference result is indicative of whether the material sample is defective.

In accordance with a third aspect of the present invention, there is provided an apparatus for testing material samples for defects, comprising means for applying a test signal to the material sample, receiving means for receiving the return signal from the material sample, and analysis means for analysing the return signal to determine whether the material sample is defective, and further including selection means for selecting a frequency range to reduce the effect of potentially interfering signals.

Preferably, the selection means is arranged to select a frequency within the range 1 to 20 kHz and more preferably between 1 and 22 kHz. The selection means most preferably is arranged to select a frequency between 3 and 15 kHz or 18 and 22 kHz. Preferably, the selection means includes a bandpass filter, preferably having a very high Q.

Preferably, the analysis means includes a means arranged to take a reference signal obtained from an undefected material sample and to subtract the reference signal from the return signal, to give a difference result. Preferably, the difference result is provided to a display for viewing by a user.

Preferably, the analysis means is arranged to digitise the reference signal and the return signal and subtract the return signal from the reference signal to give a difference quantity. It is preferably arranged to provide difference quantities for a plurality of areas across the test sample. These difference quantities, known as "damage index" are preferably utilised to produce a map on the display of the damage index across the area of the test sample. The analysis means may also be arranged to filter the return signal.

The analysis means preferably is arranged to process signals digitally.

The analysis means preferably is equipped with an electronic library of response signals.

In accordance with a fourth aspect of the present invention, there is provided an apparatus for testing a material sample for defects, comprising means for applying a test signal to the material sample, a receiving means for receiving a return signal from the material sample, an analysis means for taking a reference signal obtained from a non-defective sample and subtracting the reference signal from the return signal, to give a difference result, whereby the difference result is indicative of whether the material sample is defective.

BRIEF DESCRIPTION OF THE DRAWINGS

Features and advantages of the present invention will become apparent from the following description of an embodiment thereof, by way of example only, with reference to the accompanying drawings, in which.

DETAILED DESCRIPTION OF A PREFERRED EMBODIMENT

Figure 1:
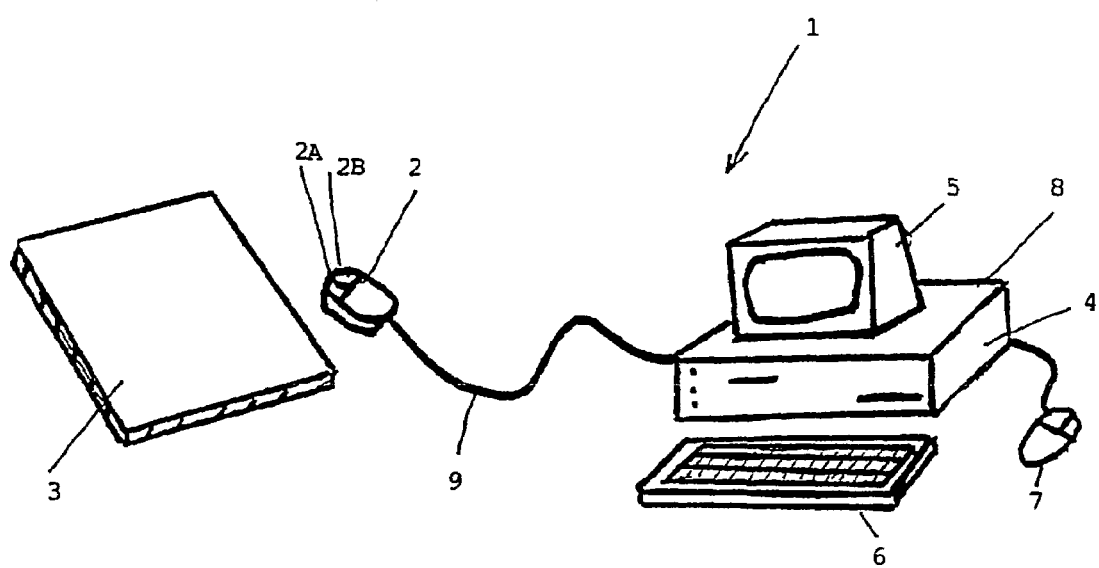
FIG. 1 is a schematic diagram of an apparatus in accordance with an embodiment of the present invention.

Referring to FIG. 1, an apparatus in accordance with an embodiment of the present invention is illustrated. The apparatus, generally designated by reference numeral 1, comprises a means 2 for applying a test signal to a composite test sample 3, and for receiving a return signal from the test sample 3. In this embodiment, the means 2 may comprise a conventional pitch/catch probe having two spring loaded contact tips set about 10 mm apart (not shown) which, in operation, are held in contact with the test piece. One of these contact tips acts as a frequency driver, and is arranged to be driven with a test signal in the acoustic to low-ultrasonic frequency range. The other contact is arranged to receive the return signal, after the signal has passed through the test sample 3.

Any conventional pitch/catch probe may be utilised as the probe 2. One probe which may be utilised is a probe developed by the present inventors and which is the subject of a co-pending patent application entitled "Probe For Non-Destructive Testing" filed on the same date as the present application, and the disclosure of which is incorporated herein by reference.

The probe 2 is connected to a means for driving the probe 2 and receiving and processing the return signal, which, in this embodiment is a computing apparatus 3 (in this case being a conventional PC programmed appropriately). The computing apparatus 3 includes a computer 4, display 5, and keyboard 6 for data entry. It also includes a mouse 7 for driving a graphical user interface (GUI).

A lead from the probe goes at least to a PCMCIA card mounted A/D convertor (not shown) for converting the return signal from the probe 2 to a digital signal. Further, a drive signal is output via the A/D converter to drive the probe 2.

Alternatively to having the drive signal output from the A/D converter, the probe may include circuitry for generating a square wave which constitutes a stepping port excitation twice in every cycle. This can be done where the ability to provide an appropriate frequency drive signal from the PC and A/D converter is not available.

It will be appreciated that sample 3 shown in FIG. 1 may be part of a larger item such as an aircraft e.g. a panel of an aircraft. Note that, practically, panels for items such as aircraft are tested in situ, so the apparatus of FIG. 1 must be transportable to be able to be used to test the item in question. A PC, for example, is easily transportable and as long as the lead 8 to the probe 2 is long enough it is easy to test items in situ with this apparatus.

In accordance with the present invention, the computing apparatus 3 is arranged to cause the probe 2 to output a drive signal which is preferably selected to be approximately 2 cycles at approximately 10 kHz. This is a fairly broadband excitation which ensures that plenty of energy is supplied to the composite test piece in the 3 to 15 kHz range. This range is chosen, as discussed above, in order to avoid the problems that have occurred in the prior art, in particular with interference from resonances due to the probe 2. However, it will be appreciated that for other materials the frequency range may be different. For example, for aluminium it has been observed that the frequency range within interfering signals are substantially reduced is within 18 to 22 kHz.

In this embodiment the received signal is bandpass filtered between in the order of 3 and 15 kHz with a very high Q filter (8 pole). In the preferred embodiment, computing apparatus 3 implements the filter by means of appropriate software processing the digitised return signal.

Note that probe 2 may also include internal electronics for applying some analogue filtering to the signal before it reaches the computing system 1. In this embodiment a 3 to 17 kHz bandpass 4 pole filter is applied in the probe 2. This assists in eliminating problems due to resonance and also acts as an anti-aliasing filter.

The bandpass filtering eliminates both low frequency noise from environmental structural sources and all probe 2 resonances above 15 kHz and leaves a range where there is a minimum overlap of defect and probe response.

At least 10 cycles of the return waveform signal are digitised so as to give a complete frequency response in the bandpass region.

A reference signal is provided by sampling an area of undefected sample. In operation, where aircraft panels are being tested, for example, the reference sample may be taken from an area of aircraft panel which is known to be undefected. A similar waveform is digitised from the region of "good" panel and stored by the computing apparatus 3. In accordance with the present invention, the reference signal is subtracted from the return signal, to give a difference result which is indicative of whether there are any defects in the test sample 3.

In this embodiment, the fast Fourier transform is computed for both the return signal waveform and the reference signal waveform. The integrated difference between the two waveforms, in either time or frequency space, is calculated by summing the absolute value of the point by point difference over the whole or sum user selected part of the waveform. This yields a single number for each sample position on the test piece, referred to here as the "damage index".

In operation, a plurality of return signals are taken by passing the probe 2 over the test sample 3 at a plurality of points on the test sample 3. The damage index for each point is then presented on display 5 as a "map" for viewing for a user.

In order to produce the map, positional information of the position of the probe 2 on the sample 3 is required. In conventional prior art methods this probe position information is obtained by attaching a part of a track or gantry to the probe which provides a readout of the measuring position. The prior art method may be employed here. Alternatively, the positional information may be obtained by utilising the inventive probe described in the applicants co-pending patent application which is referenced above.

Figure 8:
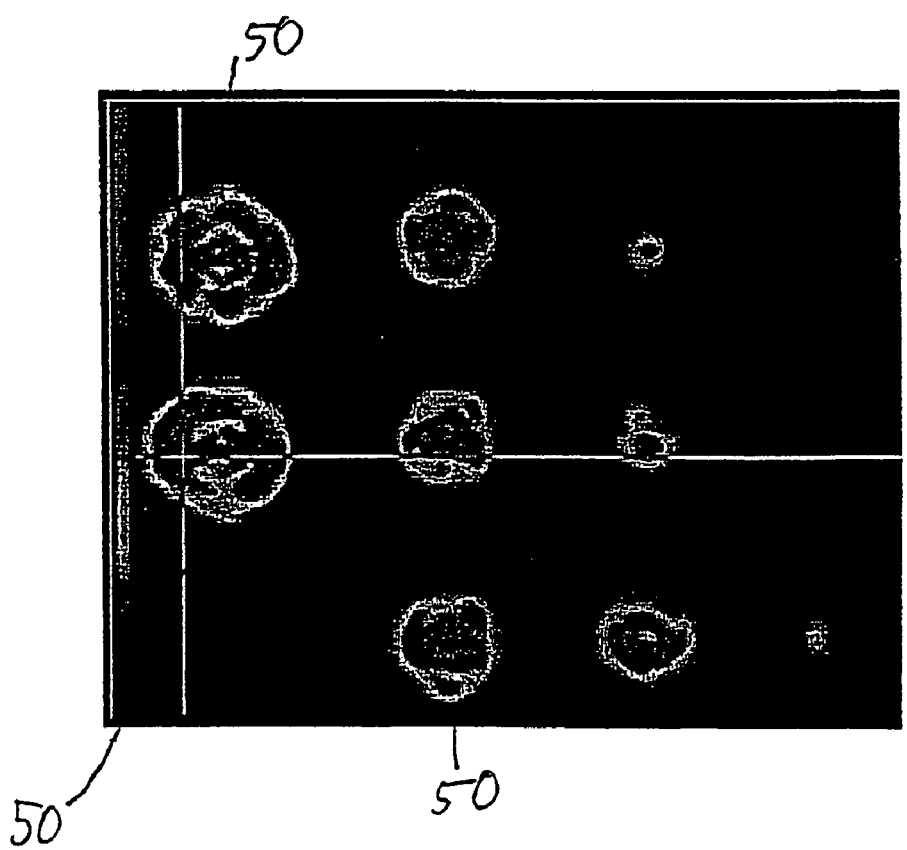
FIG. 8 is a representation of a map representing the damage index over a surface area of test sample.

FIG. 8 illustrates an example damage index map which may be displayed on the monitor 5 of the PC 3. Areas of damage are indicated by reference numerals 50.

Figure 2:
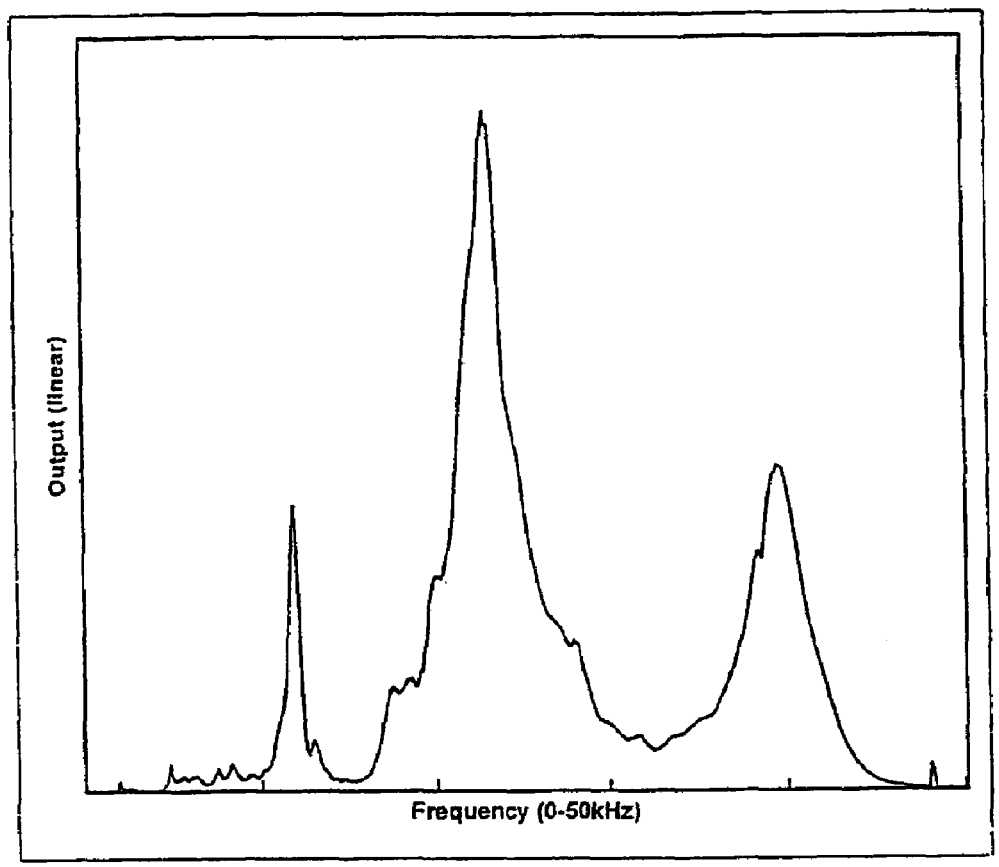
FIG. 2 is a representation of a broadband response (intensity versus frequency) of a typical NDT signal associated with a defect area of a test sample.

FIG. 1 is a representation of a broadband response of a typical signal associated with a defect area of a test sample and FIG. 2 is a representation of a broadband response of a typical signal associated with a reference area (or reference sample). As can be seen both signals have relatively high intensities between approximately 13 and 45 kHz. These large signals are believe mainly to relate to resonance responses arising from non-defective areas in the probe housing.

Figure 3:
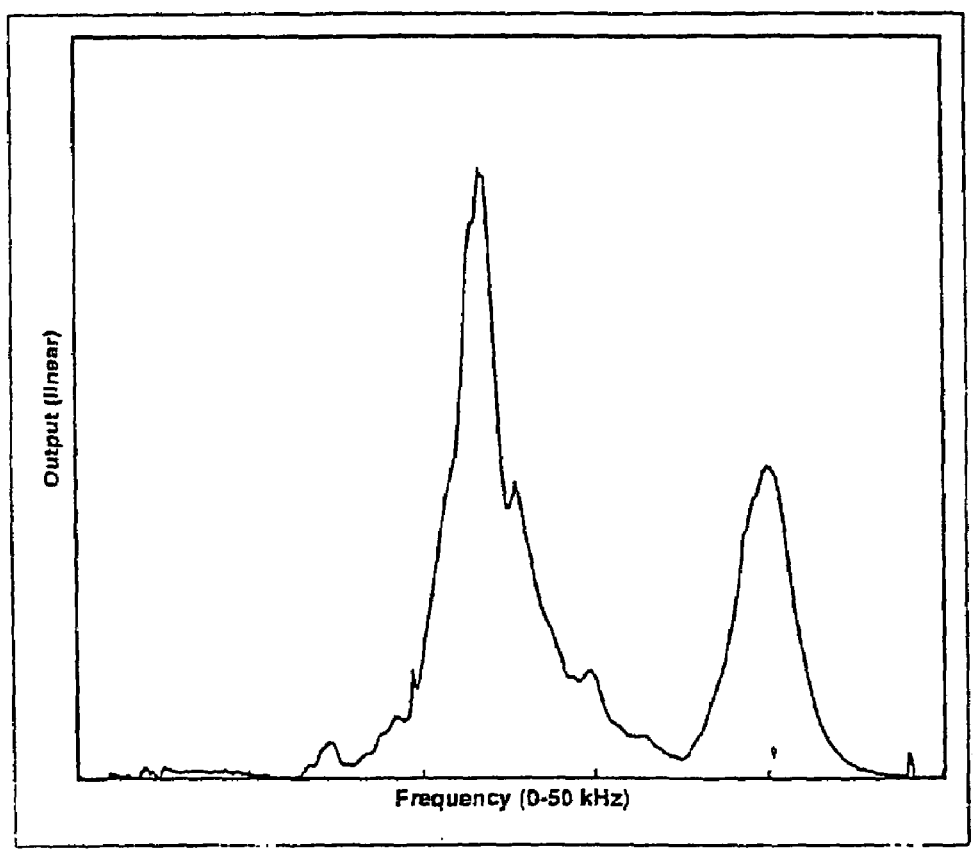
FIG. 3 is a representation of a broadband response (intensity versus frequency) of a typical NDT signal associated with an undefected sample (a reference signal)
Figure 4:
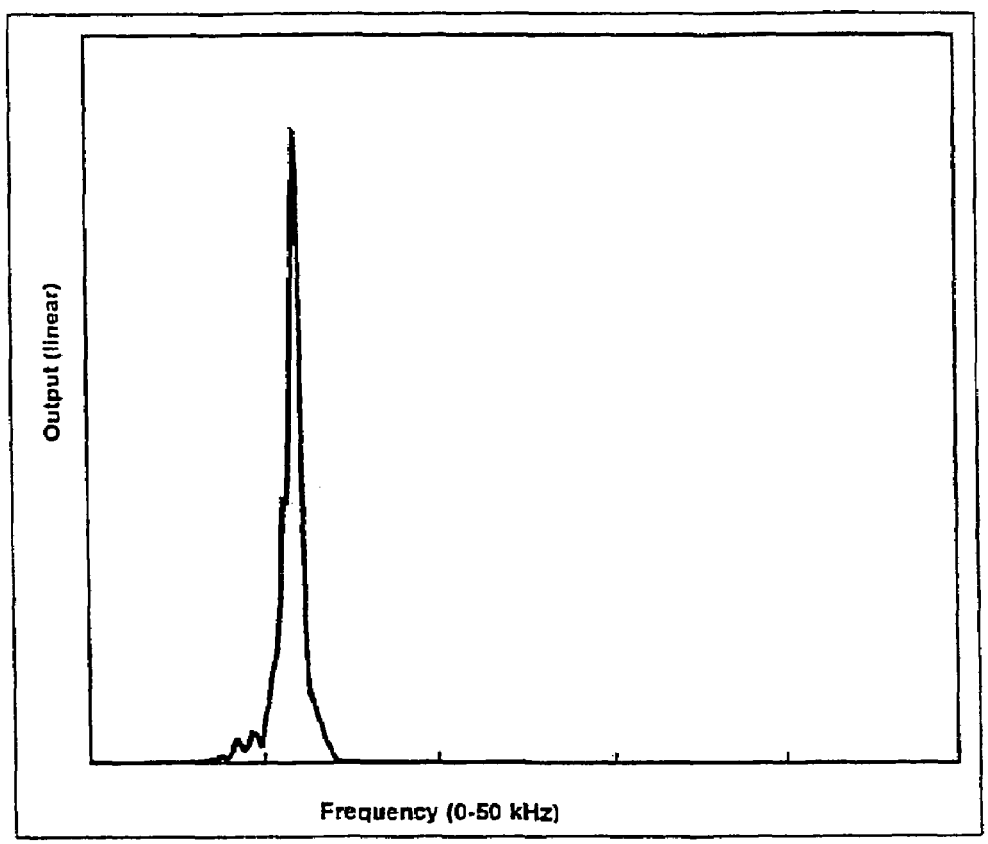
FIG. 4 is a representation of a broadband response (intensity versus frequency) of a typical defect signal after frequency filtering using a bandpass filter with a transmission of approximately 3 kHz to 15 kHz.
Figure 5:
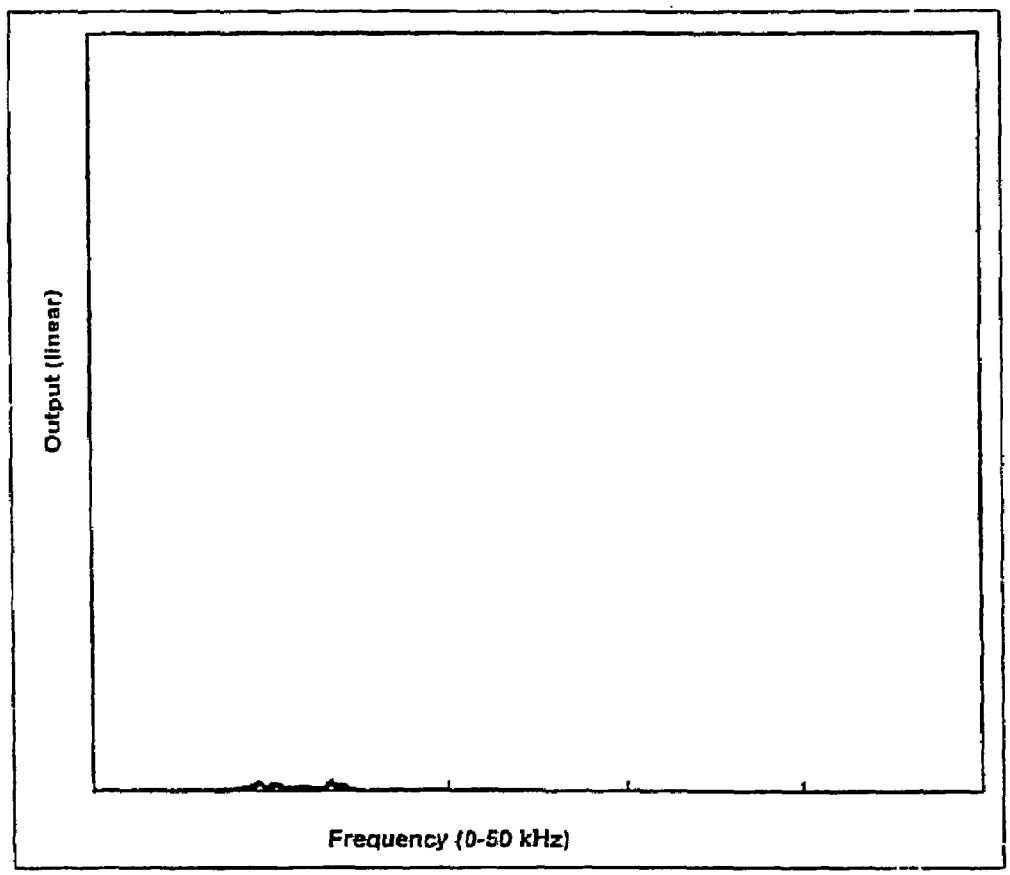
FIG. 5 is a representation of a broadband response (intensity versus frequency) of a typical reference signal after frequency filtering using a bandpass filter with a transmission of approximately 3 kHz to 15 kHz.
Figure 6:
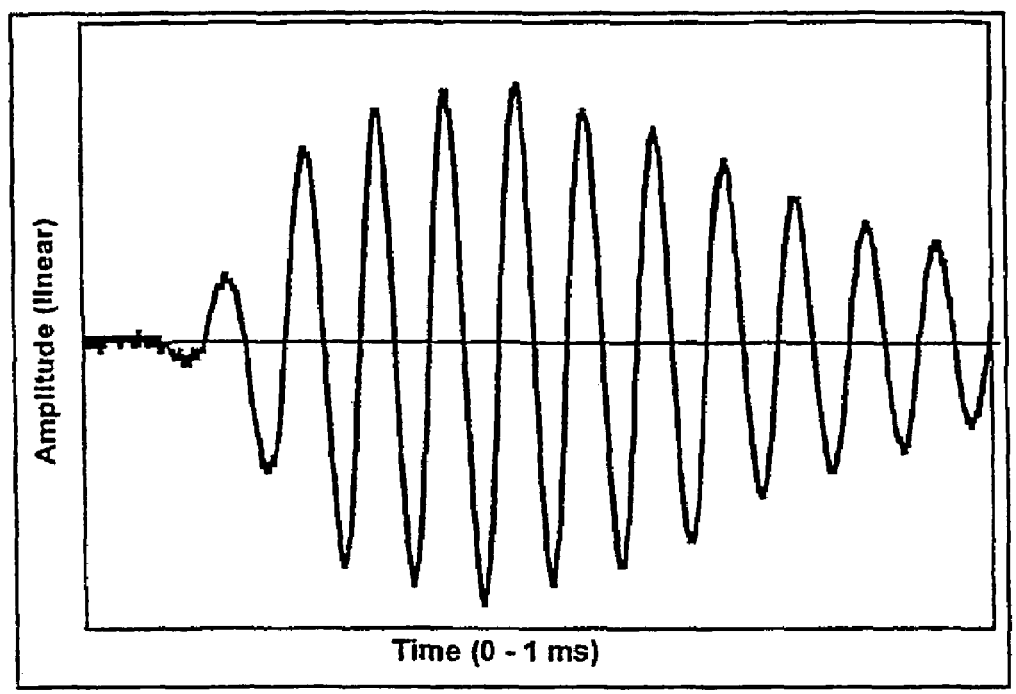
FIG. 6 is a representation of a frequency filtered defect signal (voltage versus time)
Figure 7:
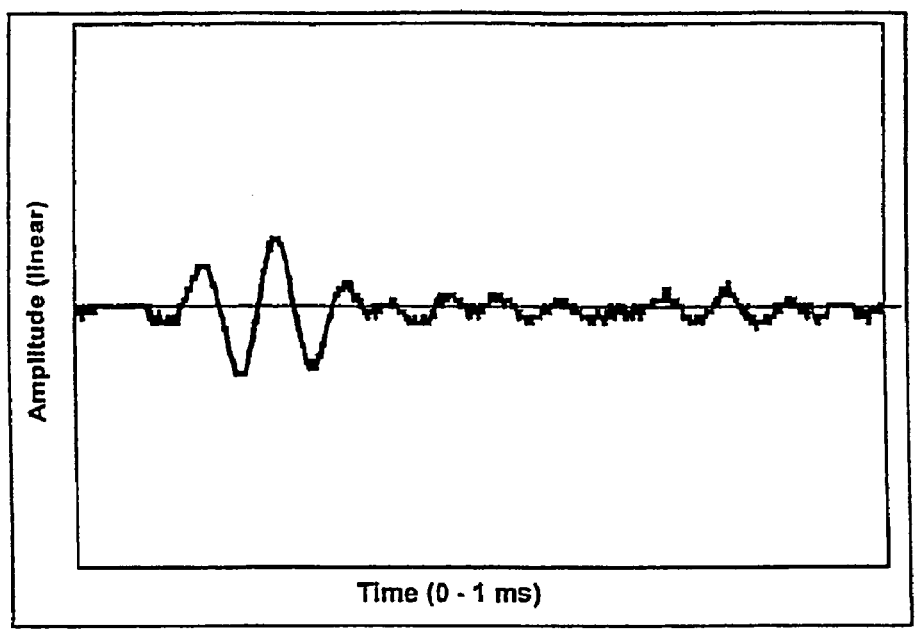
FIG. 7 is a representation of a frequency filtered reference signal (voltage versus time)

In accordance with the present invention, utilising the high Q (8 pole) frequency filter with a transmission of approximately 3 kHz to 15 kHz results, for a typical composite sample, in defect and reference signals as shown in the examples of FIGS. 3 and 4. As can be seen from these figures, the defects signal in FIG. 3 has significantly higher relative intensity compared with the reference signal of FIG. 5. FIGS. 6 and 7 show the corresponding frequency filtered NDT defective reference signals, respectively, in the time domain.

The restriction of NDT signal processing to the frequency range 3 kHz to 15 kHz for typical composite materials therefore, preferably addresses problems associated with extracting often relatively small defect signal from a signal with a relatively large overall intensity.

The present invention has been described above as being particularly suitable for use with non-destructive testing of composite materials such as used in aircraft construction. It will be appreciated, however, that the NDT method and apparatus of the present invention may be used for testing other types of materials where it is suited, and is not limited to the testing of composite materials, and is not limited to the testing of aircraft structures.

The invention could be used for testing many different types of materials.

The present invention is not limited to the use of a pitch/catch probe. Other types of probes may be utilised, such as ultrasonic pulse echo probes, eddy current probes, and others.

In the above embodiment, the filtering which is applied to select the return signal is done by way of computer software. It will be appreciated that a hardware filter may implement filtering, and the present invention is not limited to filtering by software.

The apparatus of the present invention is implemented utilising a conventional PC. It will be appreciated that it may be implemented utilising any computing system or even hardware, and is not limited to being implemented using a PC.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of non-destructive testing a material sample for defects, comprising the steps of:
   providing a probe for non-destructive testing of the material sample,
   applying an acoustic test signal to the material sample,
   receiving a return signal from the material sample, selecting an acoustic frequency range in which the probe has none or reduced inherent resonant vibrations, and
   analysing the waveform of the return signal to determine if the material sample is defective,
   wherein the return signal is analyzed within the selected frequency range whereby an overlap of a defect signal and a resonant vibration of the robe is reduced and defects can be determined more accurately.

2. A method in accordance with claim 1, wherein the frequency range selected is between 1 and 22 kHz.

3. A method in accordance with claim 2, wherein the frequency range selected is between 3 and 15 kHz.

4. A method in accordance with claim 2, wherein the frequency range selected is between 18 and 22 kHz.

5. A method in accordance with claim 1, wherein the step of selecting a frequency is implemented by filtering the return signal.

6. A method in accordance with claim 1, comprising the further step of taking a reference signal which has been obtained from a non-defective sample, subtracting the reference signal from the return signal, to give a difference result.

7. A method in accordance with claim 6, wherein the difference result is provided as a difference number which is calculated by summing the absolute value of the point by point difference over the whole or same user selected part of the return signal versus the reference signal.

8. A method in accordance with claim 7, comprising the further step of utilising the difference result to produce a display of the difference result in relation to position on the test sample.

9. An apparatus for conducting a method of non-destructive testing of a material sample for defects, the apparatus having components for conducting the method according to claim 1.

10. An apparatus in accordance with claim 9, comprising a frequency selection is component arranged to select a frequency of between 1 and 22 kHz.

11. An apparatus in accordance with claim 10, wherein the frequency selection component is arranged to select a frequency of between 3 and 15 kHz.

12. An apparatus in accordance with claim 10, wherein the frequency selection component is arranged to select a frequency of between 18 and 22 kHz.

13. An apparatus in accordance with claim 9, being arranged to take a reference signal obtained from an undetected material sample and to substrate the reference signal from the return signal, to give a difference result.

14. An apparatus in accordance with claim 9, further comprising a display means for displaying the difference result.

* * * * *